US010058332B2

(12) United States Patent
Tada

(10) Patent No.: US 10,058,332 B2
(45) Date of Patent: Aug. 28, 2018

(54) METHOD FOR TREATMENT OF CHRONIC OBSTRUCTIVE PULMONARY DISEASE

(71) Applicant: TERUMO KABUSHIKI KAISHA, Shibuya-ku (JP)

(72) Inventor: Yuichi Tada, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 640 days.

(21) Appl. No.: 13/956,193

(22) Filed: Jul. 31, 2013

(65) Prior Publication Data

US 2014/0039467 A1 Feb. 6, 2014

Related U.S. Application Data

(60) Provisional application No. 61/678,455, filed on Aug. 1, 2012.

(51) Int. Cl.
| | | |
|---|---|---|
| A61B 17/12 | (2006.01) | |
| A61M 27/00 | (2006.01) | |
| A61B 17/34 | (2006.01) | |
| A61B 17/00 | (2006.01) | |
| A61B 90/00 | (2016.01) | |

(52) U.S. Cl.
CPC .... *A61B 17/12104* (2013.01); *A61B 17/1204* (2013.01); *A61B 17/12031* (2013.01); *A61B 17/12136* (2013.01); *A61B 17/12159* (2013.01); *A61M 27/00* (2013.01); *A61B 17/3474* (2013.01); *A61B 2017/00809* (2013.01); *A61B 2017/1205* (2013.01); *A61B 2090/064* (2016.02)

(58) Field of Classification Search
CPC ............... A61B 17/12; A61B 17/1204; A61B 17/12104; A61B 17/3474; A61B 2017/00809; A61M 16/00; A61M 31/00; A61M 37/00; A61M 39/00
See application file for complete search history.

(56) References Cited

U.S. PATENT DOCUMENTS

| | | | |
|---|---|---|---|
| 6,692,494 B1 * | 2/2004 | Cooper | ..................... A61B 8/12 128/898 |
| 7,670,373 B1 * | 3/2010 | Sabanathan et al. | ............. 623/9 |
| 2003/0070682 A1 * | 4/2003 | Wilson | ................... A61F 2/2412 128/207.16 |
| 2003/0228344 A1 * | 12/2003 | Fields | ........................ A61F 2/04 424/423 |
| 2005/0096529 A1 | 5/2005 | Cooper et al. | |
| 2006/0124126 A1 * | 6/2006 | Tanaka | ................... A61M 16/00 128/200.26 |
| 2008/0115790 A1 | 5/2008 | Tanaka | |
| 2008/0121237 A1 | 5/2008 | Tanaka | |
| 2008/0127982 A1 | 6/2008 | Chang et al. | |
| 2008/0127983 A1 | 6/2008 | Chang et al. | |
| 2008/0188809 A1 | 9/2008 | Tanaka et al. | |

(Continued)

FOREIGN PATENT DOCUMENTS

| | | | |
|---|---|---|---|
| WO | WO 01/010314 A1 | 2/2001 | |
| WO | WO 2009/105455 A1 | 8/2009 | |

*Primary Examiner* — Peter S Vasat
(74) *Attorney, Agent, or Firm* — Buchanan Ingersoll & Rooney PC

(57) ABSTRACT

A method for treatment of chronic obstructive pulmonary disease includes occluding at least one of a bronchial tube and emphysema, and deciding whether or not a bypass has been formed by the occlusion.

18 Claims, 14 Drawing Sheets

(56) References Cited

U.S. PATENT DOCUMENTS

| | | |
|---|---|---|
| 2008/0188824 A1 | 9/2008 | Tanaka et al. |
| 2008/0281151 A1 | 11/2008 | Chang et al. |
| 2008/0281295 A1 | 11/2008 | Chang et al. |
| 2008/0281433 A1 | 11/2008 | Chang et al. |
| 2008/0283065 A1 | 11/2008 | Chang et al. |
| 2008/0287878 A1 | 11/2008 | Tanaka |
| 2008/0287973 A1 | 11/2008 | Aster et al. |
| 2008/0295829 A1 | 12/2008 | Evens |
| 2009/0205641 A1 | 9/2009 | Tanaka |
| 2009/0205643 A1 | 9/2009 | Tanaka et al. |
| 2009/0205644 A1 | 9/2009 | Tanaka et al. |
| 2009/0205645 A1 | 9/2009 | Tanaka et al. |
| 2009/0205646 A1 | 9/2009 | Tanaka et al. |
| 2009/0205647 A1 | 9/2009 | Plough et al. |
| 2009/0205648 A1 | 9/2009 | Tanaka et al. |
| 2009/0205649 A1 | 9/2009 | Tanaka et al. |
| 2009/0205650 A1 | 9/2009 | Tanaka et al. |
| 2009/0205651 A1 | 9/2009 | Tanaka et al. |
| 2009/0205658 A1 | 9/2009 | Tanaka et al. |
| 2009/0205665 A1 | 9/2009 | Tanaka et al. |
| 2009/0209856 A1 | 9/2009 | Tanaka et al. |
| 2009/0209906 A1 | 9/2009 | Tanaka et al. |
| 2009/0209909 A1 | 9/2009 | Tanaka et al. |
| 2009/0209917 A1 | 9/2009 | Tanaka et al. |
| 2009/0209924 A1 | 9/2009 | Tanaka |
| 2009/0209936 A1 | 9/2009 | Tanaka et al. |
| 2009/0209970 A1 | 9/2009 | Tanaka et al. |
| 2009/0209971 A1 | 9/2009 | Tanaka et al. |
| 2010/0129420 A1 | 5/2010 | Tanaka |
| 2010/0147294 A1 | 6/2010 | Chang et al. |
| 2010/0147295 A1 | 6/2010 | Chang et al. |
| 2010/0170507 A1 | 7/2010 | Tanaka et al. |
| 2010/0204707 A1 | 8/2010 | Tanaka et al. |
| 2010/0286544 A1 | 11/2010 | Tanaka et al. |
| 2011/0118669 A1 | 5/2011 | Tanaka et al. |
| 2011/0137295 A1 | 6/2011 | Tanaka |
| 2011/0180064 A1 | 7/2011 | Tanaka et al. |
| 2011/0208167 A1 | 8/2011 | Tanaka |
| 2011/0306935 A1 | 12/2011 | Tanaka et al. |
| 2012/0102879 A1 | 5/2012 | Tanaka et al. |
| 2012/0103853 A1 | 5/2012 | Tanaka et al. |
| 2012/0277584 A1 | 11/2012 | Tanaka et al. |
| 2013/0072910 A1 | 3/2013 | Tanaka |

\* cited by examiner

METHOD FOR TREATMENT OF CHRONIC OBSTRUCTIVE PULMONARY DISEASE

The entire disclosure of U.S. Provisional Application No. 61/678,455 filed Aug. 1, 2012 is expressly incorporated by reference herein.

BACKGROUND OF THE INVENTION

1. Field of the Invention

The present invention relates to a method for treatment of chronic obstructive pulmonary disease.

2. Description of Related Art

In recent years, a disease called COPD (Chronic Obstructive Pulmonary Disease) has been known. The COPD is a generic term for diseases in which the airway comes to remain occluded over a long time, such as chronic bronchitis and pulmonary emphysema. In the case where chronic inflammation occurs with a lesion in a peripheral airway as an incipient lesion and the inflammation evolves to the peripheral side, so-called emphysema such as destruction of alveoli takes place.

As a method for treatment of COPD, there is a technique called airway bypass, in which air stagnating in a site (lesion part) of emphysema or the like due to a disease is guided to other site through an airway or airways other than the bronchial tube. As the airway bypass, there has been known a procedure in which a vent hole offering communication between the exterior of the patient's body and the inside of lung parenchyma is formed in a patient's chest so that air accumulated in the lung parenchyma is let escape to the exterior through the vent hole (see, for example, Document 1: WO 2009/105455 A1).

Besides, reserve flow paths called bypasses can exist in the lung parenchyma, in addition to the bronchial tubes (see, for example, Document 2: WO 01/010314 A1). Therefore, if a bypass or bypasses are formed and function, air stagnating in a lesion part is sent to the airway bypass and is guided through the airway bypass to the exterior of the patient's body.

However, the bypasses do not always function in the vicinity of the lesion part. Therefore, there may be cases where the air in the lesion part is not sent to the airway bypass and, hence, the airway bypass effect cannot be obtained.

SUMMARY OF THE INVENTION

It is an object of the present invention to provide a method for treatment of chronic obstructive pulmonary disease by which an airway bypass effect can be obtained.

According to the present invention, there is provided a method for treatment of chronic obstructive pulmonary disease which includes occluding at least one of a bronchial tube and emphysema; and deciding whether or not a bypass has been formed by the occlusion.

In accordance with the present invention, at least one of the bronchial tube and the emphysema is occluded. This makes it possible to raise the carbon dioxide partial pressure in that region inclusive of the emphysema which is governed by the bronchial tube, and to compress the tissues in the periphery of the lesion part. Therefore, it is made easy for the bypass or bypasses in the vicinity of the lesion part to function. Consequently, the air in the lesion part can be securely sent to the airway bypass, and the airway bypass effect can be obtained sufficiently.

According to the present invention, there is provided a method for treatment of chronic obstructive pulmonary disease, including: occluding at least one of a bronchial tube and emphysema so as to form a bypass; and releasing the occlusion.

In accordance with the present invention, the bypass or bypasses can be formed in the vicinity of the lesion part by occluding at least one of the bronchial tube and the emphysema. This ensures that the air in the lesion part can be assuredly sent to the airway bypass, and the airway bypass effect can be obtained sufficiently. Furthermore, since the occlusion is released, a situation in which a burden is kept imposed on the lesion part after the bypass formation can be avoided.

In the method for treatment of chronic obstructive pulmonary disease according to the present invention, preferably, at least one of the bronchial tube and the emphysema is occluded by putting a plugging element indwelling in the bronchial tube.

In accordance with the present invention, the bronchial tube and the emphysema in connection with the bronchial tube are occluded by putting the plugging element indwelling in the bronchial tube. This eliminates the need for a treatment instrument such as a catheter to be kept connected to the patient in effecting the occlusion. Therefore, the burden on the patient during the treatment can be lessened.

In the method for treatment of chronic obstructive pulmonary disease according to the present invention, preferably, at least one of the bronchial tube and the emphysema is occluded by expanding an expansion body in the emphysema.

In accordance with the present invention, the emphysema is occluded by expanding the expansion body in the emphysema. Therefore, it is possible to interrupt the supply of air from the bronchial tube to the emphysema, and thereby to raise the carbon dioxide partial pressure in the emphysema. In addition, it is possible to compress the tissues surrounding the emphysema. This permits the bypass or bypasses to function more easily, so that the airway bypass effect can be enhanced.

In the method for treatment of chronic obstructive pulmonary disease according to the present invention, preferably, removing the plugging element to release the occlusion is conducted after deciding whether or not the bypass has been formed.

In accordance with the present invention, removing the plugging element to release the occlusion is performed after deciding whether or not the bypass has been formed. This makes it possible to release the occlusion after it is confirmed that the bypass or bypasses have been formed. Here, since the lesion part such as the emphysema is not being occluded with the plugging element, the decision of whether or not the bypass has been formed in the vicinity of the lesion part can be made even with the plugging element left indwelling. Therefore, the treatment can be completed after the effect of the bypass or bypasses is confirmed. Consequently, the treatment can be carried out more assuredly.

In the method for treatment of chronic obstructive pulmonary disease according to the present invention, preferably, removing the expansion body to release the occlusion is conducted before deciding whether or not the bypass has been formed.

In accordance with the present invention, the expansion body is removed to release the occlusion before deciding whether or not the bypass has been formed. This ensures that the expansion body can be prevented from obstructing the decision.

In the method for treatment of chronic obstructive pulmonary disease according to the present invention, preferably, a patient's chest is provided with a vent hole which pierces a thorax and communicates with the inside of lung parenchyma, and introducing a gas through the vent hole into an occluded bronchial tube or emphysema is conducted after occluding at least one of the bronchial tube and the emphysema.

In accordance with the present invention, the gas is introduced through the vent hole into the occluded bronchial tube or emphysema. This makes it possible to compress the tissues in the periphery of the emphysema and thereby to exert a load on the peripheral tissues. As a result, it can be made easier for the bypass or bypasses to function, and, therefore, the airway bypass effect can be further enhanced.

DETAILED DESCRIPTION OF THE PREFERRED EMBODIMENT(S)

Figure 1:
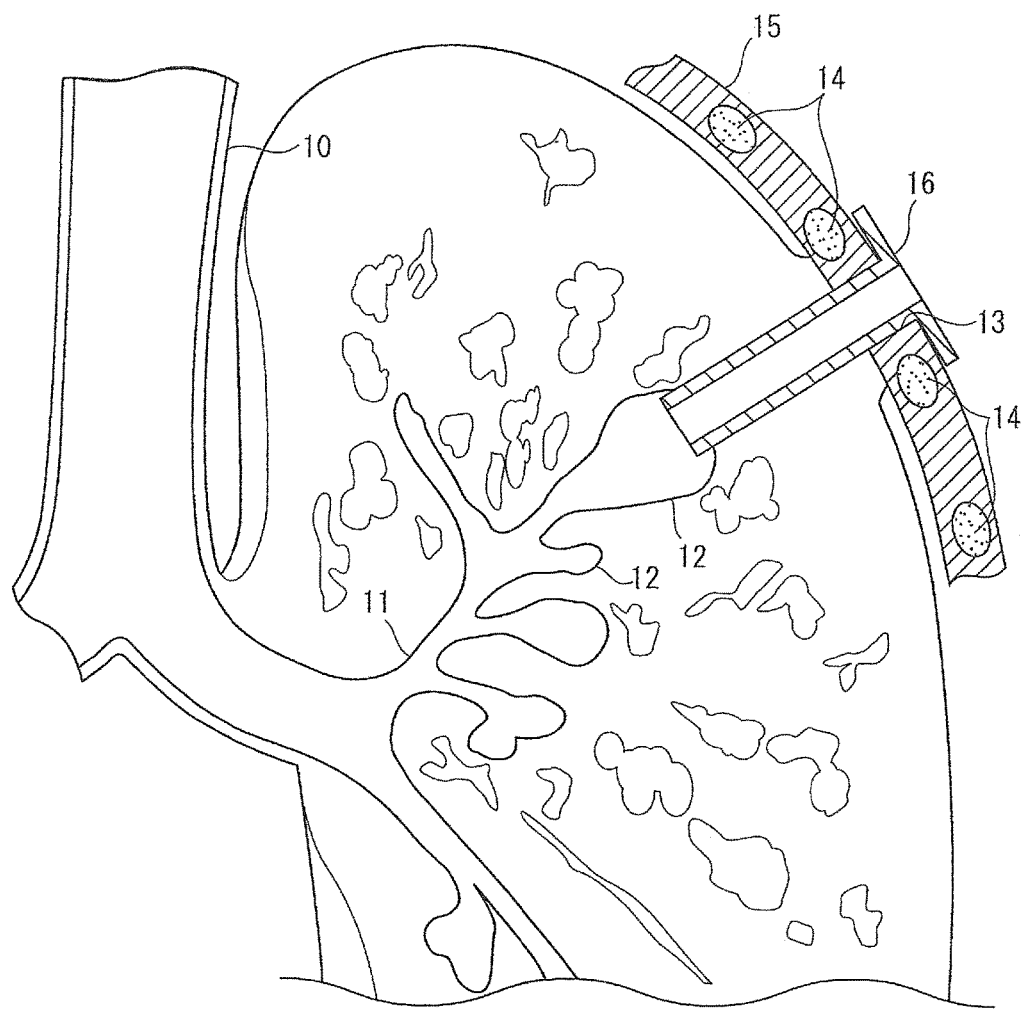
FIG. 1 is a drawing illustrating the state inside lung parenchyma of a patient suffering from COPD.

Now, some embodiments of the present invention will be described below, referring to the drawings.

Incidentally, in the second and latter embodiments, the same component members as the component members in the first embodiment and component members having the same or equivalent functions to those of the component members in the first embodiment will be denoted by the same reference signs used in the first embodiment, and descriptions of them will be omitted or simplified.

First Embodiment

FIG. 1 is a drawing which illustrates the state inside lung parenchyma of a patient suffering from COPD.

In FIG. 1, bronchial tubes 11 branched from a trachea 10 and emphysema (lesion part) 12 where air is stagnant due to a disease are present in the patient's lung parenchyma. In addition, the patient's chest is formed with a vent hole 13 as an airway bypass for treatment of COPD, by way of which the exterior of the patient's body and the lung parenchyma are interconnected. The vent hole 13 is formed to pierce a thorax 15, a parietal pleura, and a visceral pleura between costal bones 14, and communicates emphysema 12 in the lung parenchyma. Here, the parietal pleura and the visceral pleura are adhered to each other, and the vent hole 13 is formed in the adhered part. In the vent hole 13 is inserted a vent port 16 for preventing the vent hole 13 from being occluded. A distal portion of the vent port 16 is reaching the inside of the emphysema 12.

Here, bypasses can exist in the lung parenchyma. However, the airway resistance in the bypasses is very high (in a normal lung, about 50 times the ordinary airway resistance). Even in the case of a COPD patient, therefore, the bypasses do not always function. It is known, in addition, that even if bypasses are functioning, the bypasses do not always function in the vicinity of a lesion part such as the emphysema 12.

Figure 2:
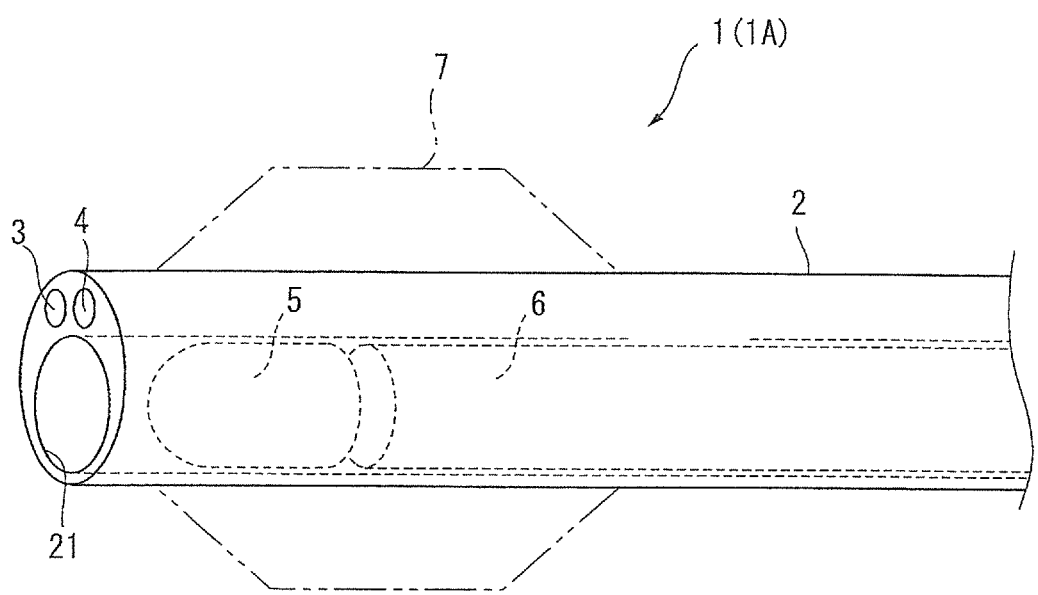
FIG. 2 is a perspective view showing an example of a treatment instrument for use in a first embodiment of the present invention.

FIG. 2 is a perspective view showing an example of a treatment instrument for use in treatment of COPD.

In FIG. 2, the treatment instrument 1 includes: a flexible insertion tube 2 having a lumen 21 opening at the distal end of the treatment instrument 1; an image sensing part 3 such as a CCD (Charge Coupled Device) image sensor provided at a distal portion of the insertion tube 2; and a light transmission part 4 such as an optical fiber for transmitting light toward the distal portion of the treatment instrument 1. The treatment instrument 1 is so configured that a plugging element 5 can be accommodated in the lumen 21 and that the plugging element 5 can be pushed out by a pushing member 6. Incidentally, for the plugging element 5, an arbitrary material and an arbitrary shape can be adopted.

Figure 3:
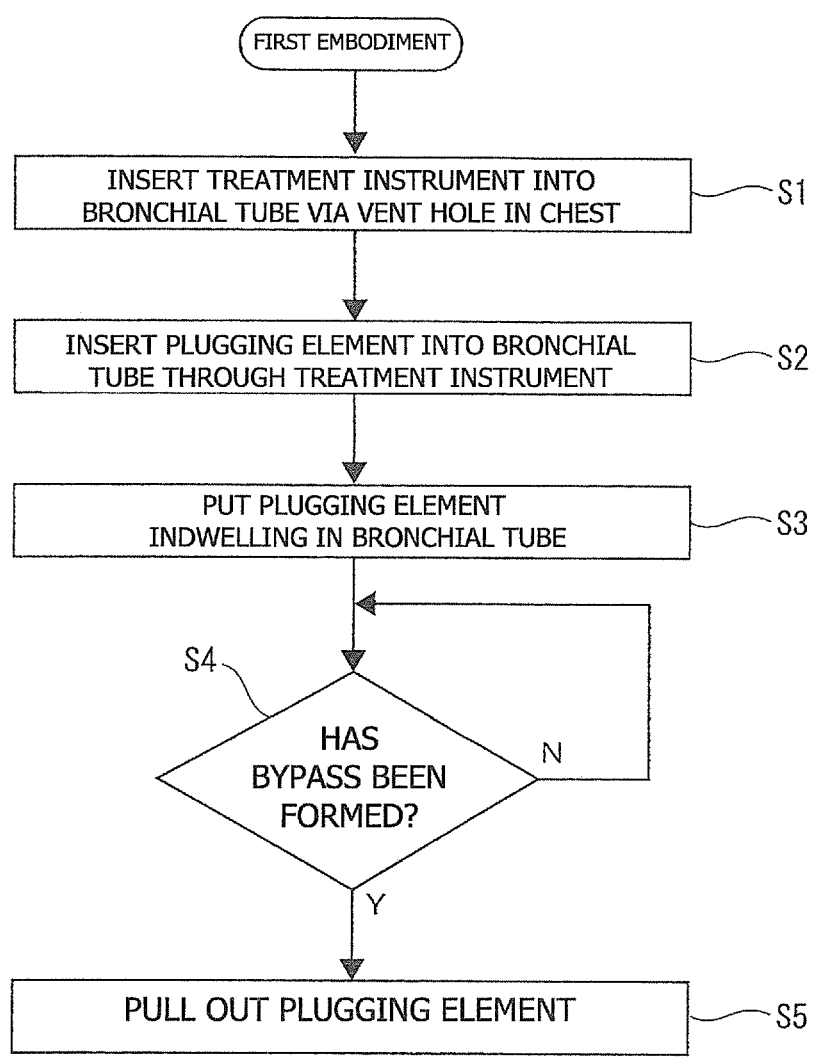
FIG. 3 shows a flow chart for a treatment according to the first embodiment.

Now, the method for treatment according to the present embodiment will be described below, along the steps in the flow chart shown in FIG. 3.

Figure 4:
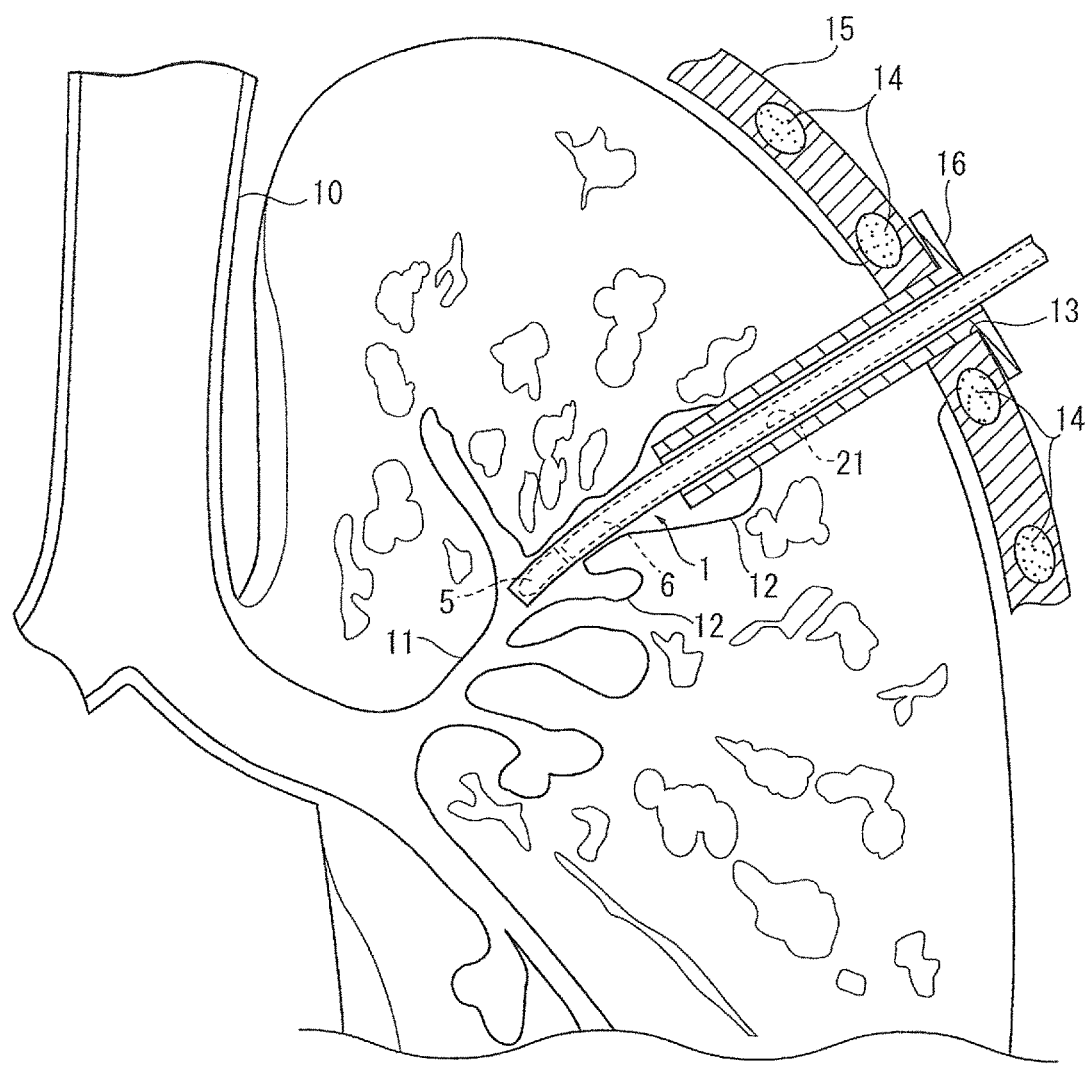
FIG. 4 is a drawing illustrating the treatment according to the first embodiment.

First, as shown in FIG. 4, the surgeon inserts the treatment instrument 1, with the plugging element 5 accommodated therein, from the vent hole 13 into the bronchial tube 11 through the vent port 16 (Step S1). In this instance, the surgeon can insert the treatment instrument 1 by checking the state inside the lung parenchyma, based on the image information acquired by the image sensing part 3.

Figure 5:
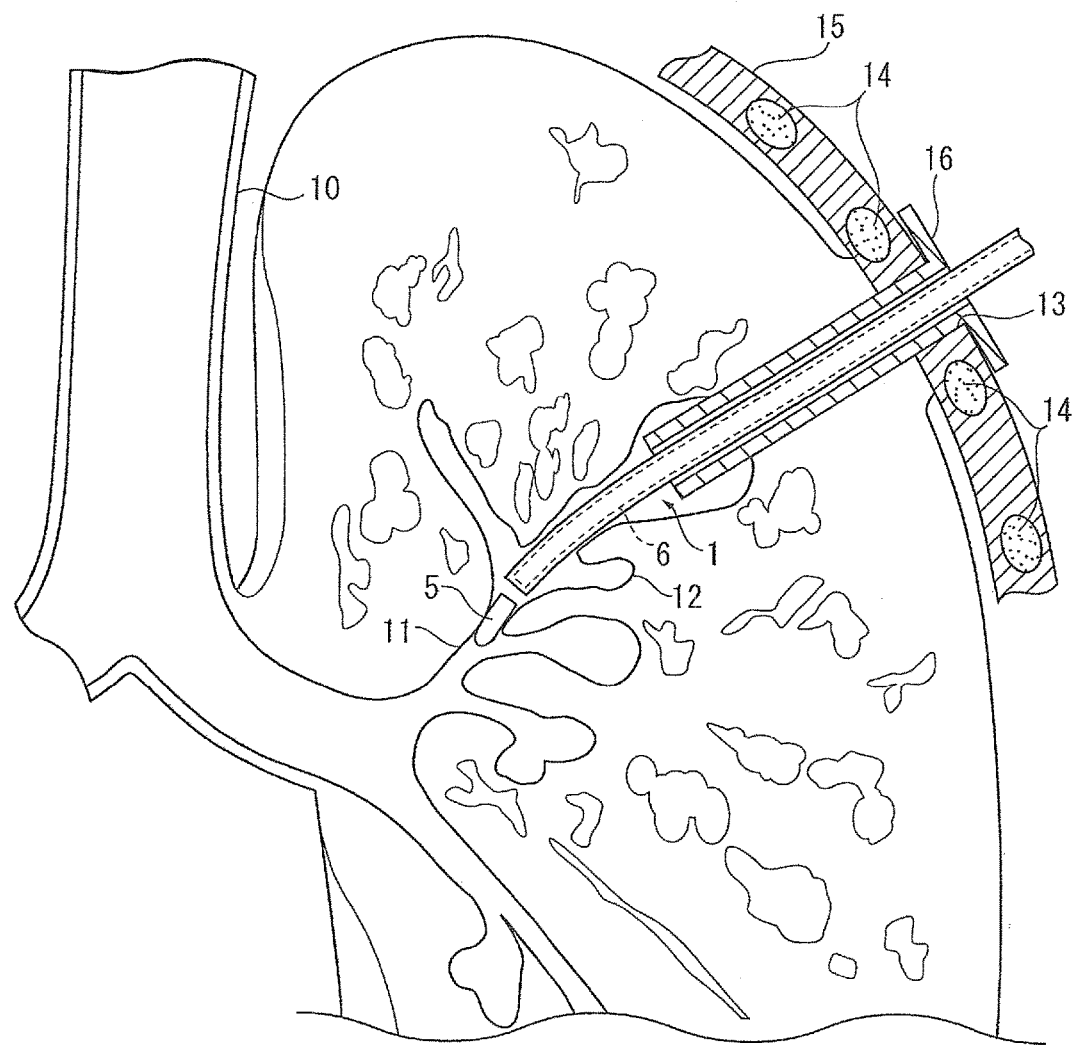
FIG. 5 is a drawing illustrating the treatment according to the first embodiment.

Next, as shown in FIG. 5, the plugging element 5 is pushed out by the pushing member 6, whereby the plugging element 5 is inserted into the bronchial tube 11 (Step S2).

Figure 6:
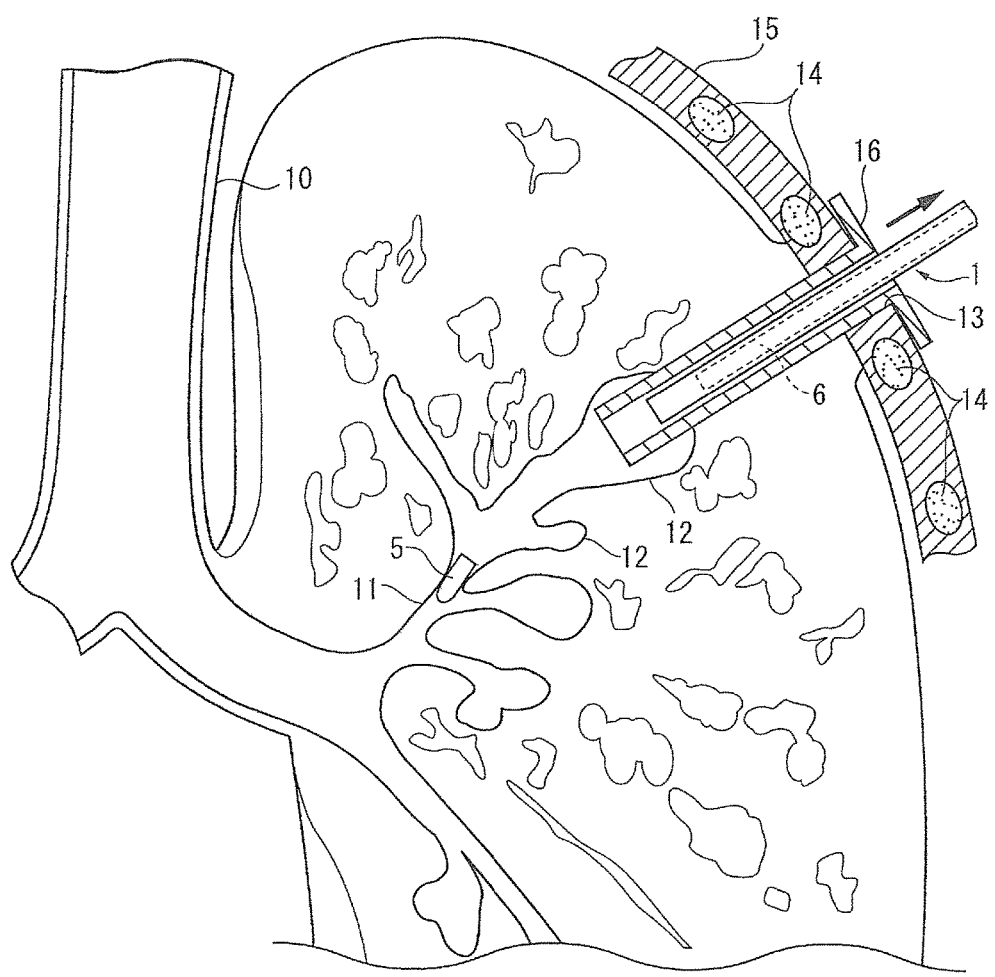
FIG. 6 is a drawing illustrating the treatment according to the first embodiment.

Then, as shown in FIG. 6, the treatment instrument 1 and the pushing member 6 are pulled out, while the plugging element 5 is left indwelling in the bronchial tube 11 (Step S3). As a result, the bronchial tube 11 and the emphysema 12 in connection with the bronchial tube 11 are occluded. Therefore, an alveolar hypoventilation state is intentionally created, and the carbon dioxide partial pressure in that region inclusive of the emphysema 12 which is governed by the bronchial tube 11 is raised. Accordingly, it is made easier for bypasses to be formed, and the airway resistance against the air passing through the bypasses can be lowered. Consequently, it can be made easier for the bypasses to function.

Thereafter, it is checked whether or not a bypass or bypasses have been formed, namely, whether or not a bypass or bypasses are functioning (Step S4). As a method for this checking, the description in the above-mentioned Document 2 is cited.

Figure 7:
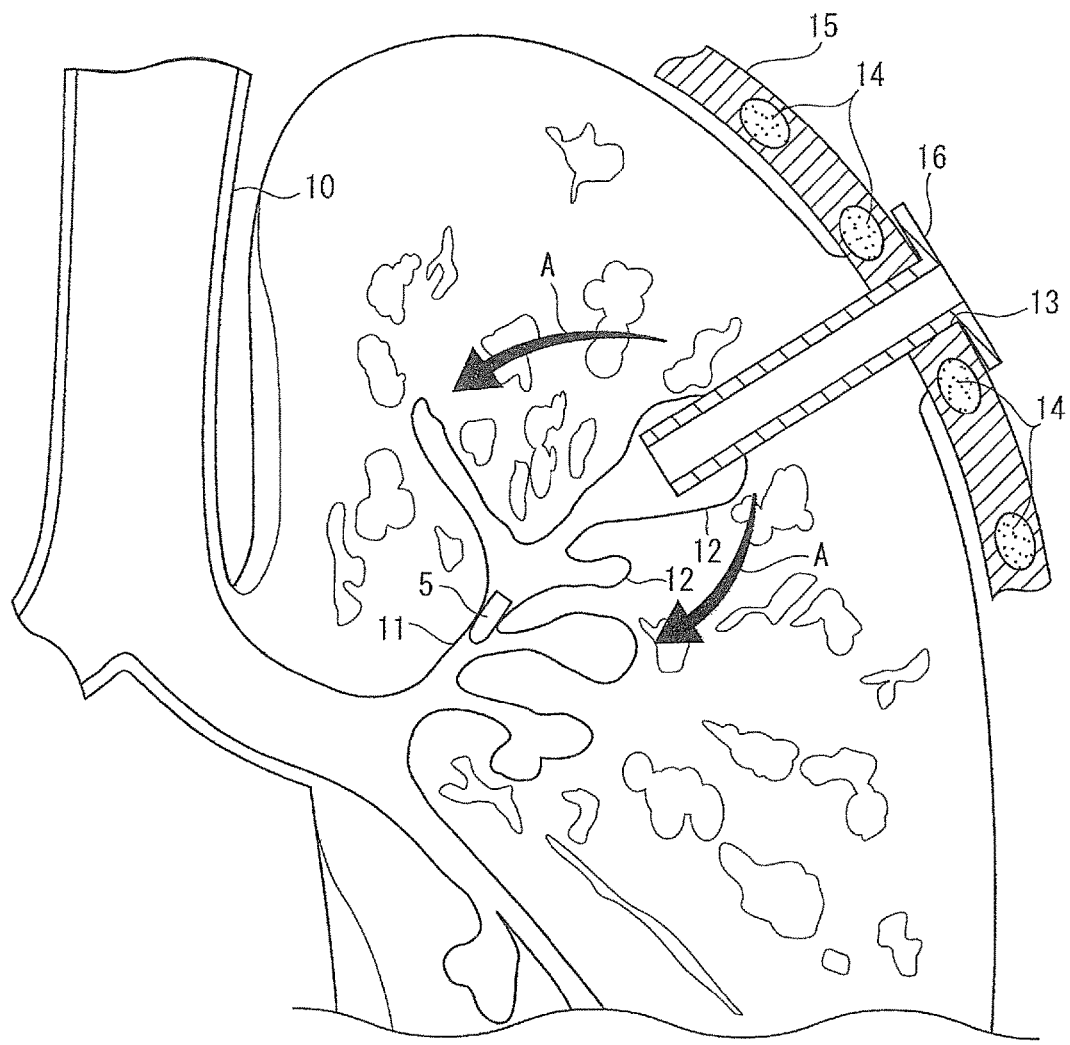
FIG. 7 is a drawing illustrating the treatment according to the first embodiment.

When it is confirmed that a bypass or bypasses have been formed, as indicated by arrows A in FIG. 7, the plugging element 5 is pulled out (Step S5). As a result, the occlusion by the plugging element 5 is released. Incidentally, it generally takes a few weeks for a bypass or bypasses to be formed and to function.

According to the present embodiment, the following effect is produced.

Since at least one of the bronchial tube 11 and the emphysema 12 is occluded, the carbon dioxide partial pressure in that region inclusive of the emphysema 12 which is governed by the bronchial tube 11 can be raised. Therefore, it can be made easier for a bypass or bypasses to function in the vicinity of the lesion. Consequently, air in the lesion part can be securely sent to the vent hole 13, and the airway bypass effect can be obtained sufficiently.

In addition, the bronchial tube 11 and the emphysema 12 in connection therewith are occluded by the plugging element 5 set indwelling in the bronchial tube 11. Therefore, it is unnecessary to keep the treatment instrument 1 connected to the patient, in realizing the occlusion. Accordingly, the burden on the patient during the treatment can be alleviated.

Second Embodiment

Figure 8:
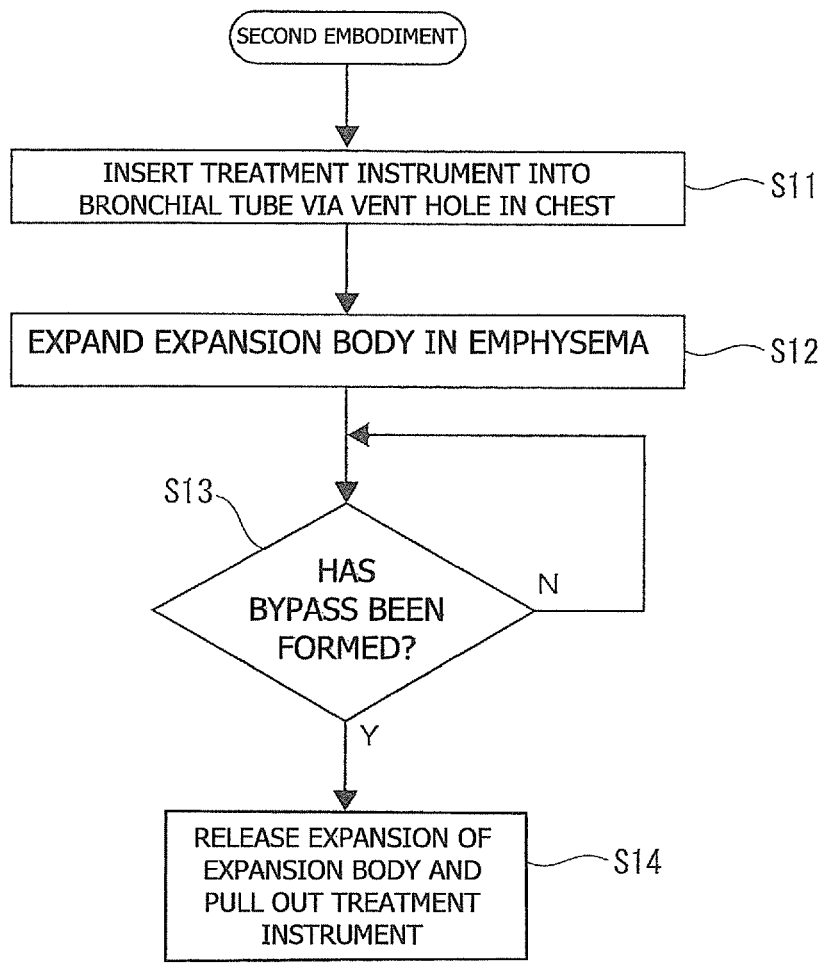
FIG. 8 shows a flow chart for a treatment according to a second embodiment of the present invention.

Now, a second embodiment of the present invention will be described below, based on FIGS. 8 to 10.

The present embodiment differs from the first embodiment in that a bypass or bypasses are formed by expanding an expansion body 7 in emphysema 12.

The method for treatment according to the present embodiment will now be described below, along the steps in the flow chart shown in FIG. 8.

Figure 9:
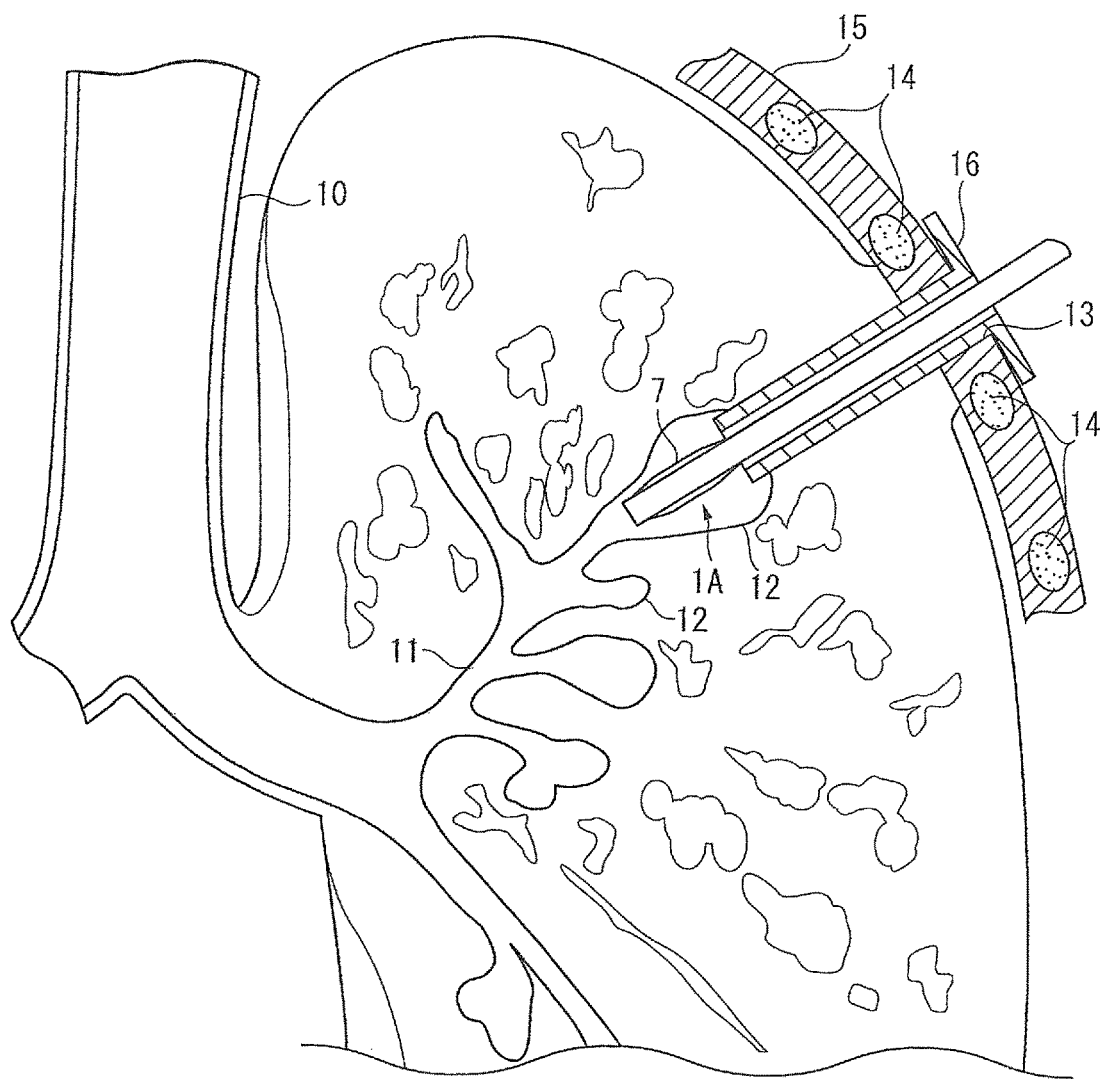
FIG. 9 is a drawing illustrating the treatment according to the second embodiment.

First, as shown in FIG. 9, the surgeon inserts a treatment instrument 1A from a vent hole 13 into the emphysema 12 through a vent port 16 (Step S11). Incidentally, as indicated by two-dot chain line in FIG. 2, the treatment instrument 1A has a configuration in which the expansion body 7 is provided on the outer circumference of a distal portion of an insertion tube 2 of the treatment instrument 1.

Figure 10:
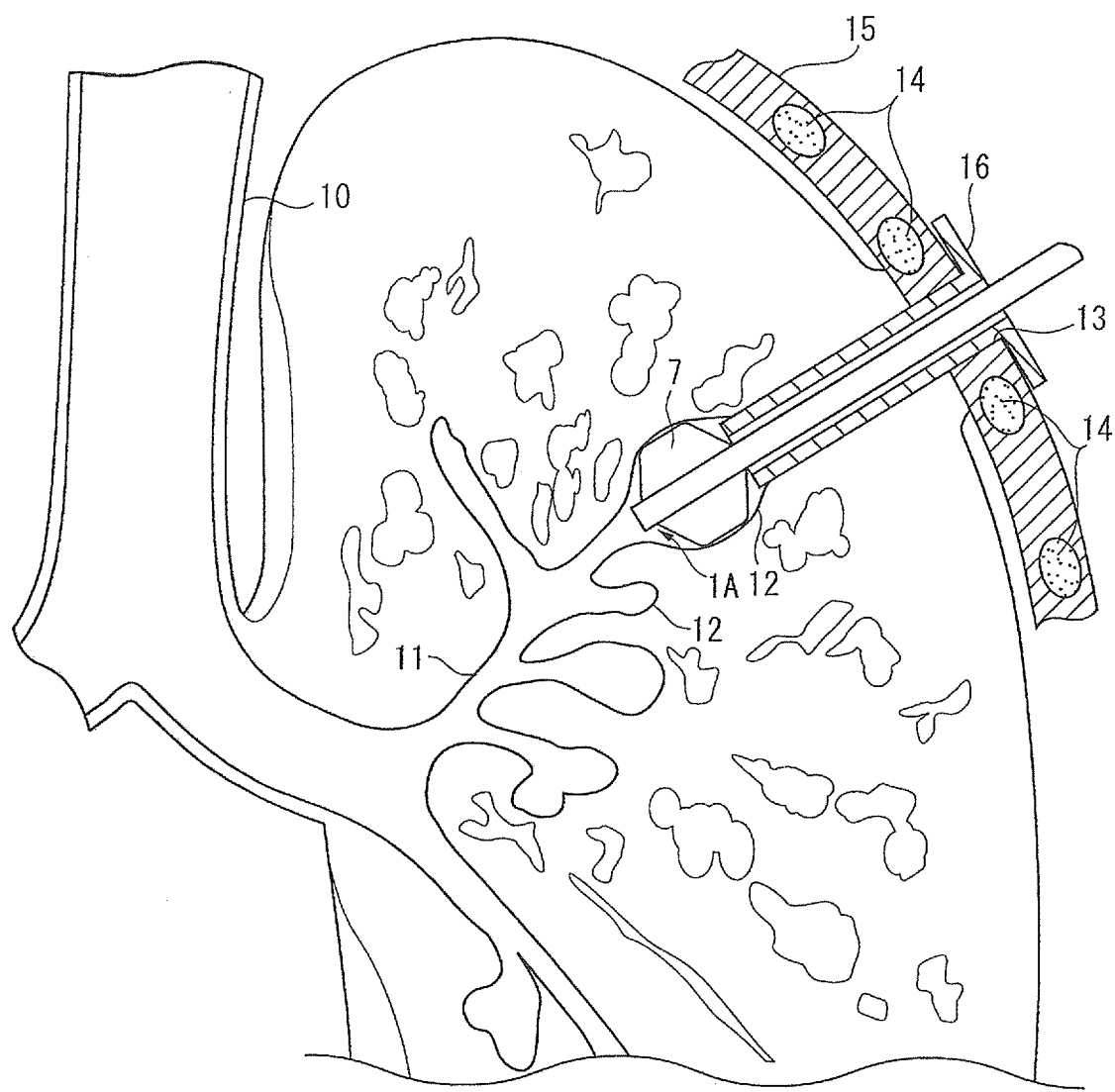
FIG. 10 is a drawing illustrating the treatment according to the second embodiment.

Then, as shown in FIG. 10, the expansion body 7 is expanded in the condition where the expansion body 7 is located in the emphysema 12 (Step S12). As a result, the emphysema 12 is occluded, and the internal volume of the emphysema 12 is reduced. In addition, the tissues in the periphery of the emphysema 12 are compressed. Therefore, the supply of fresh air from a bronchial tube 11 to the emphysema 12 is interrupted, and carbon dioxide in blood is released, resulting in a rise in the concentration of carbon dioxide. Thus, there results a condition for a bypass or bypasses to be easily formed, and for the bypass or bypasses to easily function. Incidentally, the concentration of carbon dioxide may be artificially raised, by injection of carbon dioxide through the gap between the treatment instrument 1A and the vent port 16.

Thereafter, it is checked whether or not a bypass or bypasses have been formed (Step S13). When it is confirmed that a bypass or bypasses have been formed and are functioning, the expansion of the expansion body 7 is released, and the treatment instrument 1A is pulled out (Step S14). Incidentally, in the case where it is difficult to check the formation of a bypass or bypasses while the expansion body 7 is located in the emphysema 12, the formation of a bypass or bypasses can be checked after the expansion body 7 is contracted and the treatment instrument 1A is pulled out.

According to the present embodiment, the following effect is produced.

Since the emphysema 12 is occluded by expanding the expansion body 7 in the emphysema 12, it is possible to interrupt the supply of air from the bronchial tube 11 to the emphysema 12, thereby raising the concentration of carbon dioxide in the emphysema 12. Besides, it is possible to compress the tissues surrounding the emphysema 12. This permits a bypass or bypasses to function easily, and, consequently, the airway bypass effect can be enhanced.

Third Embodiment

Now, a third embodiment of the present invention will be described below, referring to FIGS. 11 to 13.

The present embodiment differs from the first embodiment in that a bypass or bypasses are formed by introducing a gas into emphysema 12 after a plugging element 5 is set indwelling in a bronchial tube 11.

Figure 11:
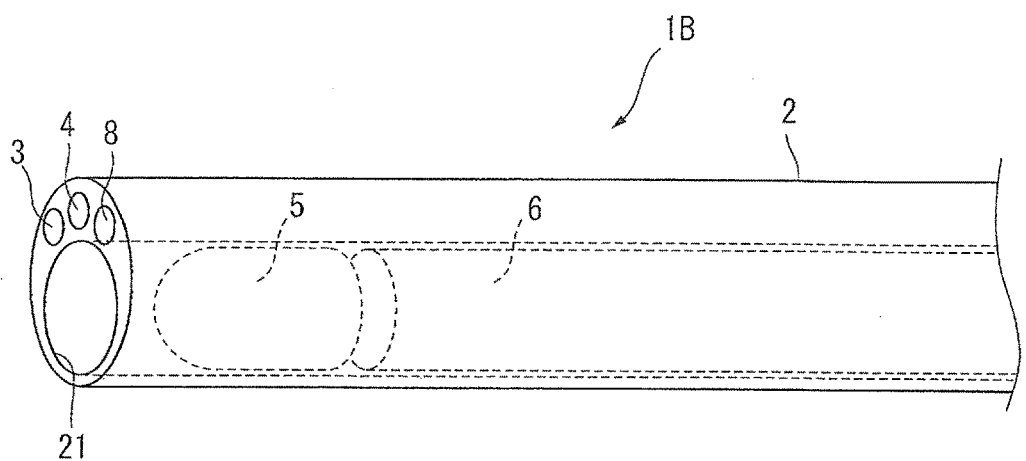
FIG. 11 is a perspective view showing an example of a treatment instrument for use in a third embodiment of the present invention.
Figure 12:
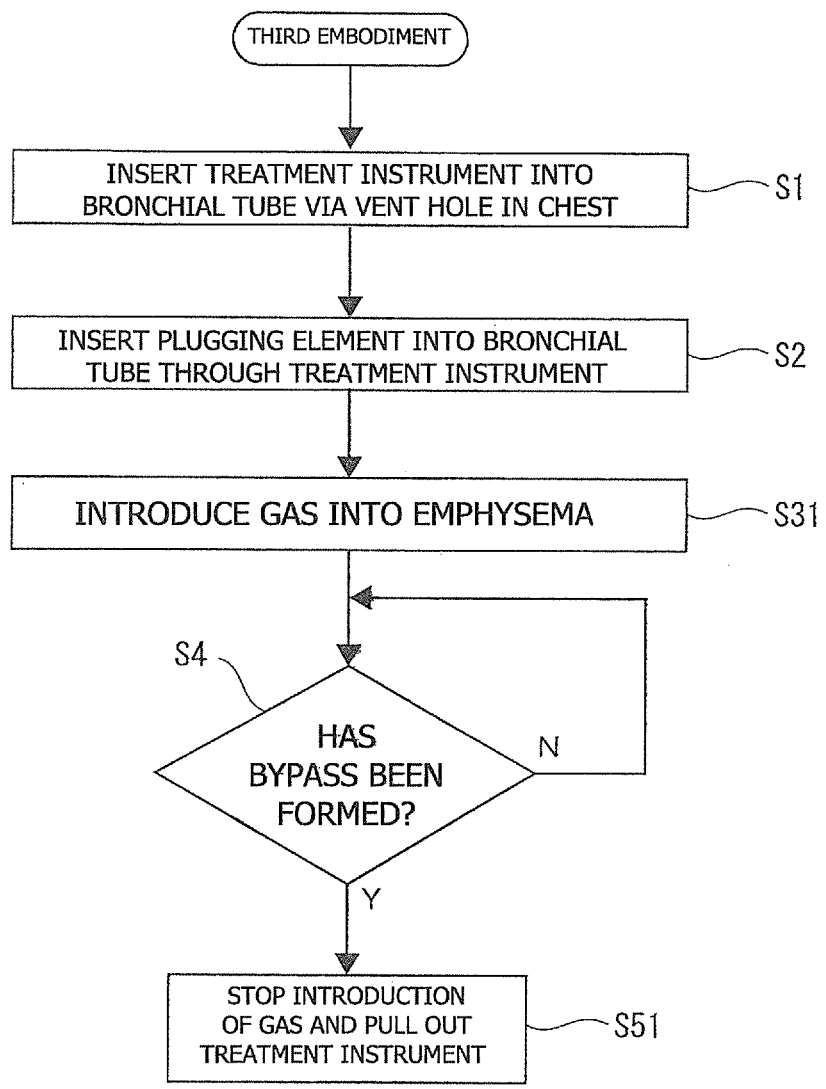
FIG. 12 shows a flow chart for a treatment according to the third embodiment.

FIG. 11 is a perspective view showing an example of a treatment instrument for use in the present embodiment.

In FIG. 11, the treatment instrument 1B has a configuration wherein a pressure sensor 8 is provided at a distal portion of an insertion tube 2 of the treatment instrument 1 (FIG. 2). Like the treatment instrument 1, the treatment instrument 1B is so configured that a plugging element 5 can be accommodated in its lumen 21 and that the plugging element 5 can be pushed out by a pushing member 6. In addition, the treatment instrument 1B may be provided with an expansion body, like the treatment instrument 1A (FIG. 2).

The method for treatment according to the present embodiment will now be described below, along the steps in the flow chart shown in FIG. 12. Incidentally, Steps S1 and S2 are the same as those in the first embodiment, except that the plugging element 5 is set indwelling in the bronchial tube 11 at the entrance to the emphysema 12. Therefore, the steps subsequent to Step S2 will be described below.

Figure 13:
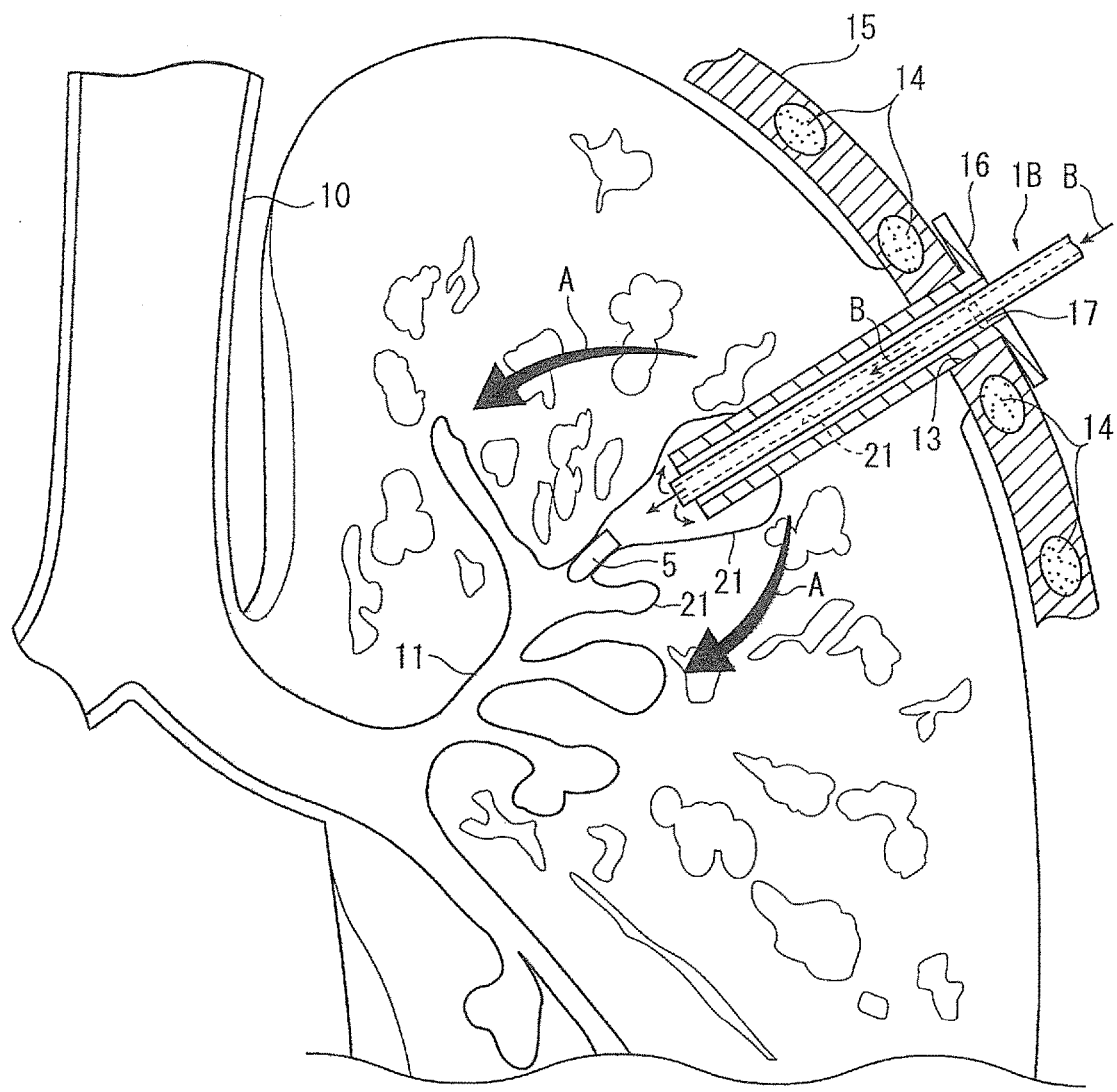
FIG. 13 is a drawing illustrating the treatment according to the third embodiment.

After the plugging element 5 is inserted into the bronchial tube 11 to occlude the emphysema 12, the surgeon introduces a gas into the emphysema 12 through the lumen 21 of the treatment instrument 1B, as indicated by arrows B in FIG. 13 (Step S31). In this instance, the surgeon can introduce the gas into the emphysema 12 while checking the pressure condition in the emphysema 12, based on a pressure value measured by the pressure sensor 8.

Here, an annular seal member 17 is provided inside the vent port 16 so that the introduced gas would not leak via the gap between the vent port 16 and the treatment instrument 1B. Therefore, with the gas introduced into the emphysema 12, the tissues in the periphery of the emphysema 12 are compressed, and a load is exerted on the peripheral tissues. This permits a bypass or bypasses to be easily formed, and enables the bypass or bypasses to function easily. While examples of the gas to be introduced include carbon dioxide, an arbitrary gas can be adopted so long as the gas permits the bypass or bypasses to function.

Thereafter, it is checked whether or not a bypass or bypasses have been formed (Step S4). When it is confirmed that a bypass or bypasses have been formed and are functioning, as indicated by arrows A in FIG. 13, the introduction of the gas into the emphysema 12 is stopped, and the plugging element 5 is pulled out (Step S51).

According to the present embodiment, the following effect is produced in addition to the effect of the first embodiment.

Since the gas is introduced from the vent hole 13 into the occluded emphysema 12, the tissues in the periphery of the emphysema 12 can be compressed, and a load can be applied to the peripheral tissues. Therefore, it is made possible for the bypass or bypasses to function more easily, and the airway bypass effect can be further enhanced.

Incidentally, the present invention is not restricted to the above-described embodiments, and modifications and improvements and the like within such ranges that the object of the present invention can be attained are embraced in the present invention.

Figure 14:
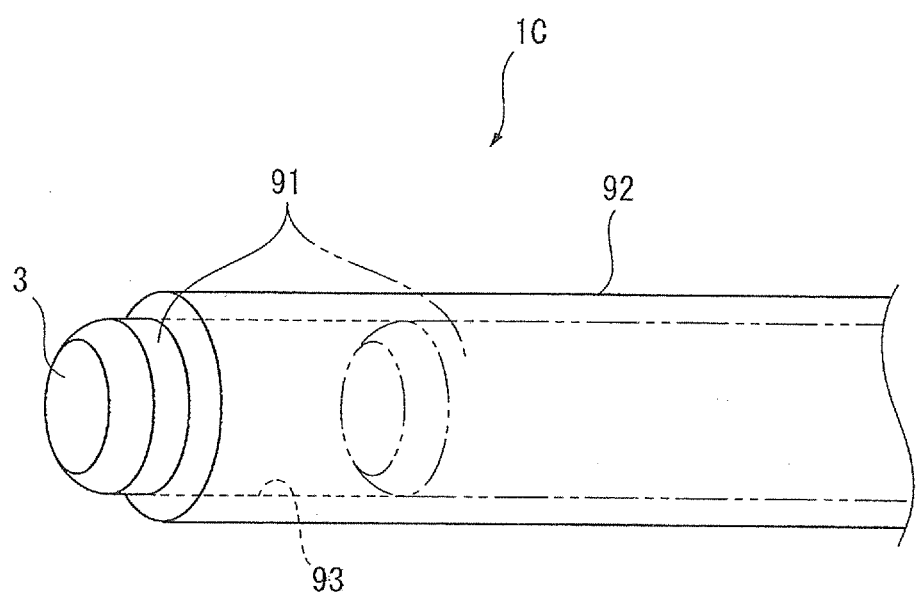
FIG. 14 is a perspective view showing a modification of the treatment instrument according to each of the embodiments.

For instance, while the treatment instruments 1, 1A and 1B are provided with the image sensing part 3 at a distal portion of the insertion tube 2 in the above-described embodiments, the configuration of the treatment instruments 1, 1A and 1B is not restricted to this one. For example, as shown in FIG. 14, an insertion member 91 provided with an image sensing part 3 at a distal portion thereof may be provided in a lumen 93 of a flexible catheter 92, in such a manner that it can be inserted deep into and pulled out of the lumen 93, to configure a treatment instrument 1C. In this case, when the insertion member 91 is pulled out and a plugging element 5 or the like is accommodated in the catheter 92, it is unnecessary to provide the image sensing part 3 and the plugging element 5 in a juxtaposed manner in the treatment instrument 1C. As a result, the treatment instrument 1C can be made smaller in outside diameter, and, therefore, the burden on the patient at the time of inserting the treatment instrument 1C can be alleviated.

In addition, the image sensing part 3 in the treatment instruments 1, 1A, 1B and 1C is not indispensable. For instance, in the case where the insertion position for the treatment instrument 1, 1A, 1B and 1C in the lung parenchyma is in the vicinity of the vent port 16 or where the state inside the lung parenchyma can be checked externally, the treatment instrument 1, 1A, 1B and 1C may not necessarily be provided with the image sensing part 3.

While the plugging element 5, the expansion body 7, the gas and the like are inserted from the vent hole 13 into the lung parenchyma through the vent port 16 in the above-described embodiments, this is not restrictive, and the insertion may be carried out perorally or transnasally by use of a treatment instrument such as a bronchoscope.

While the occlusion is released after the decision of whether or not a bypass has been formed in the above-described embodiments, the decision of whether or not a bypass has been formed may be carried out after the occlusion is released.

In the above-described second embodiment, carbon dioxide as a gas may be artificially introduced into the gap between the emphysema and the expansion body 7, in the same manner as in the third embodiment. This ensures that the concentration of carbon dioxide is further raised and the peripheral tissues are more compressed, so that it can be made easier for the bypass or bypasses to function.

While the plugging element 5 is set indwelling in the entrance to the emphysema 12 in the above-described third embodiment, the plugging member 5 may be set indwelling in the bronchial tube 11, like in the first embodiment.

Besides, while the gas pressure inside the emphysema 12 is manually operated in the above-described third embodiment, the gas pressure may be controlled by a gas pressure controller (not shown), based on the pressure value measured by the pressure sensor 8.

Furthermore, while the seal member 17 is provided inside the vent port 16 in the above-described third embodiment, the seal member 17 may be provided on the outer circumference of the treatment instrument 1B.

While each of the above-described embodiments is applied as a method for treatment of COPD, the present invention may be applied as a method for treatment of other disease insofar as the treatment involves the need for a bypass or bypasses to be formed and let function.

What is claimed is:

1. A method for treatment of chronic obstructive pulmonary disease of a living body, wherein a vent hole pierces a thorax of the living body and communicates with inside of lung parenchyma within the living body, the method comprising:
   occluding at least one of a bronchial tube and body tissue having emphysema;
   deciding whether or not a bypass has been formed by a reaction of the living body in response to the occlusion while the vent hole is in communication with the inside of the lung parenchyma, the bypass being an air pathway that guides air between the lung parenchyma within the living body and that guides air from the lung parenchyma to the vent hole, and the bypass being not present before the occlusion of the at least one of the bronchial tube and body tissue having emphysema; and
   removing the occlusion after the bypass is formed, so that the bypass remains and passes air from the lung parenchyma within the living body out of the living body through the vent hole piercing the thorax of the living body after the occlusion is removed.

2. The method for treatment of chronic obstructive pulmonary disease according to claim 1,
   wherein at least one of the bronchial tube and the body tissue having emphysema is occluded by putting a plugging element indwelling in the bronchial tube.

3. The method for treatment of chronic obstructive pulmonary disease according to claim 2,
   wherein removing the plugging element to release the occlusion is conducted after deciding whether or not the bypass has been formed.

4. The method for treatment of chronic obstructive pulmonary disease according to claim 2, further comprising:
   introducing a gas through the vent hole into an occluded bronchial tube or body tissue having emphysema after occluding at least one of the bronchial tube and the body tissue having emphysema.

5. The method for treatment of chronic obstructive pulmonary disease according to claim 1,
   wherein at least one of the bronchial tube and the body tissue having emphysema is occluded by expanding an expansion body in the emphysema.

6. The method for treatment of chronic obstructive pulmonary disease according to claim 5,
   wherein removing the expansion body to release the occlusion is conducted before deciding whether or not the bypass has been formed.

7. The method for treatment of chronic obstructive pulmonary disease according to claim 5, further comprising:
   introducing a gas through the vent hole into an occluded bronchial tube or body tissue having emphysema after occluding at least one of the bronchial tube and the body tissue having emphysema.

8. The method for treatment of chronic obstructive pulmonary disease according to claim 1, further comprising:
   introducing a gas through the vent hole into an occluded bronchial tube or body tissue having emphysema after occluding at least one of the bronchial tube and the body tissue having emphysema.

9. The method according to claim 1, wherein the occlusion is formed by inserting a plugging element into the at least one of the bronchial tube and the body tissue having emphysema via the vent hole piercing the thorax of the living body.

10. A method for treatment of chronic obstructive pulmonary disease of a living body, wherein a vent hole pierces a thorax of the living body and communicates with inside of lung parenchyma within the living body, the method comprising:

occluding at least one of a bronchial tube and a body tissue having emphysema to form a bypass by a reaction of the living body in response to the occlusion while the vent hole is in communication with the inside of the lung parenchyma, the bypass being an air pathway that guides air between the lung parenchyma within the living body and that guides air from the lung parenchyma to the vent hole, and the bypass being not present before the occlusion of the at least one of the bronchial tube and body tissue having emphysema; and releasing the occlusion after the bypass is formed, wherein the bypass remains and guides air between the lung parenchyma within the living body and guides air from the lung parenchyma out of the living body through the vent hole piercing the thorax of the living body after the occlusion is removed.

11. The method for treatment of chronic obstructive pulmonary disease according to claim 10, wherein at least one of the bronchial tube and the body tissue having emphysema is occluded by putting a plugging element indwelling in the bronchial tube.

12. The method for treatment of chronic obstructive pulmonary disease according to claim 11, further comprising:

introducing a gas through the vent hole into an occluded bronchial tube or body tissue having emphysema after occluding at least one of the bronchial tube and the body tissue having emphysema.

13. The method for treatment of chronic obstructive pulmonary disease according to claim 10, wherein at least one of the bronchial tube and the body tissue having emphysema is occluded by expanding an expansion body in the body tissue having emphysema.

14. The method for treatment of chronic obstructive pulmonary disease according to claim 13, further comprising:

introducing a gas through the vent hole into an occluded bronchial tube or body tissue having emphysema after occluding at least one of the bronchial tube and the body tissue having emphysema.

15. The method for treatment of chronic obstructive pulmonary disease according to claim 10, further comprising:

introducing a gas through the vent hole into an occluded bronchial tube or body tissue having emphysema after occluding at least one of the bronchial tube and the body tissue having emphysema.

16. The method according to claim 10, wherein the occlusion is formed by inserting a plugging element into the at least one of the bronchial tube and the body tissue having the emphysema via the vent hole piercing the thorax of the living body.

17. A method for treatment of chronic obstructive pulmonary disease of a living body, comprising:

occluding at least one of a bronchial tube and a body tissue of the living body having emphysema to form a bypass by a reaction of the living body in response to the occlusion, the bypass being an air pathway that guides air between lung parenchyma within the living body and that guides air from the lung parenchyma to a vent hole, and the bypass being not present before the occlusion of the at least one of the bronchial tube and body tissue having emphysema; and removing the occlusion after the bypass is formed, so that the bypass remains between the lung parenchyma within the living body after the occlusion is removed.

18. The method according to claim 17, wherein the bypass guides air from the lung parenchyma out of the living body through the vent hole piercing the thorax of the living body after the occlusion is removed.

* * * * *